United States Patent [19]

Huckabee et al.

[11] Patent Number: 5,629,447
[45] Date of Patent: May 13, 1997

[54] METHODS OF MAKING (S)-3-(AMINOMETHYL)-5-METHYLHEXANOIC ACID

[75] Inventors: Brian K. Huckabee; Denis M. Sobieray, both of Holland, Mich.

[73] Assignee: Warner-Lambert Company, Morris Plains, N.J.

[21] Appl. No.: 672,783

[22] Filed: Jun. 28, 1996

Related U.S. Application Data

[62] Division of Ser. No. 458,950, Jun. 2, 1995.

[51] Int. Cl.$^6$ .................................................. C07C 205/00
[52] U.S. Cl. ............................................................ 562/553
[58] Field of Search ................................................ 562/553

[56] References Cited

U.S. PATENT DOCUMENTS

| | | | |
|---|---|---|---|
| 2,944,969 | 7/1960 | Stromberg | 562/553 |
| 3,544,467 | 12/1970 | Kautsky | 562/553 |
| 3,857,879 | 12/1974 | Abramitis | 562/553 |
| 4,123,438 | 10/1978 | Geurts et al. | 260/326.5 |
| 4,711,671 | 12/1987 | Mazzarella et al. | 106/243 |
| 4,739,114 | 4/1988 | Lee et al. | 562/524 |
| 5,136,051 | 8/1992 | Schuster et al. | 548/553 |

FOREIGN PATENT DOCUMENTS 9323383  5/1993  WIPO .

OTHER PUBLICATIONS

PCT Search Report dated Aug. 10, 1996.

Yuen, et al., *Bioorganic & Medicinal Chemistry Letters*, vol. 4, No. 6, pp. 823–826 (1994).

Andruszkiewicz, et al., *Synthetic Communications*, 20(1), pp. 159–166 (1990).

*Primary Examiner*—Michael L. Shippen
*Attorney, Agent, or Firm*—Todd M. Crissey

[57] ABSTRACT

The present invention provides a method of making (S)-(+)-3-(aminomethyl)-5-methylhexanoic acid which comprises condensing isovaleraldehyde with an alkyl cyanoacetate to form a 2-cyano-5-methylhex-2-enoic acid alkyl ester; reacting the 2-cyano-5-methylhex-2-enoic acid alkyl ester with a dialkyl malonate to form 3-isobutylglutaric acid; forming the anhydride of 3-isobutylglutaric acid; reacting the anhydride with ammonia to form (±)-3-(carbamoylmethyl)-5-methylhexanoic acid; reacting (±)-3-(carbamoylmethyl)-5-methylhexanoic acid with (R)-(+)-α-phenylethylamine to obtain the (R)-(+)-α-phenylethylamine salt of (R)-(−)-3-(carbamoylmethyl)-5-methylhexanoic acid; combining the salt with an acid to obtain (R)-(−)-3-(carbamoylmethyl)-5-methylhexanoic acid; and reacting the (R)-(−)-3-carbamoylmethyl)-5-methylhexanoic acid with a Hofmann reagent to obtain (S)-(+)-3-(amino-methyl)-5-methylhexanoic acid.

5 Claims, No Drawings

METHODS OF MAKING (S)-3-(AMINOMETHYL)-5-METHYLHEXANOIC ACID

This is a divisional of U.S. application Ser. No. 08/458,950, filed Jun. 2, 1995.

FIELD OF THE INVENTION

This invention relates to a method of making (S)-(+)-3-(aminomethyl)-5-methylhexanoic acid. This invention also relates to the compounds (±)-3-(carbamoylmethyl)-5-methylhexanoic acid, (R)-(−)-3-(carbamoylmethyl)-5-methylhexanoic acid, (S)-(+)-3-( carbamoylmethyl)-5-methylhexanoic acid, the (R)-(+)-α-phenylethylamine salt of (R)-(−)-3-(carbamoylmethyl)-5-methylhexanoic acid, and the (S)-(−)-α-phenylethylamine salt of (S)-(+)-3-(carbamoylmethyl)-5-methylhexanoic acid.

BACKGROUND OF THE INVENTION (S)-(+)-3-(aminomethyl)-5-methylhexanoic acid, which is also called β-isobutyl-γ-aminobutyric acid or isobutyl-GABA, is a potent anticonvulsant. Isobutyl-GABA is related to the endogenous inhibitory neurotransmitter γ-aminobutyric acid or GABA, which is involved in the regulation of brain neuronal activity.

It is thought that convulsions can be controlled by controlling the metabolism of the neurotransmitter γ-aminobutyric acid. When the concentration of GABA diminishes below a threshold level in the brain, convulsions result (Karlsson A., et. al., *Biochem. Pharmacol.*, 1974; 23: 3053–3061), and when the GABA level rises in the brain during convulsions, the seizures terminate (Hayashi T., *Physiol., (London)* 1959; 145: 570–578). The term "seizure" means excessive unsynchronized neuronal activity that disrupts normal function.

Because of the importance of GABA as an inhibitory neurotransmitter, and its effect on convulsive states and other motor dysfunctions, a variety of approaches have been taken to increase the concentration of GABA in the brain. In one approach, compounds that activate L-glutamic acid decarboxylase (GAD) have been used, as the concentrations of GAD and GABA vary in parallel and increased GAD concentrations result in increased GABA concentrations (Janssens de Varebeke P., et. al., *Biochem. Pharmacol.*, 1983; 32: 2751–2755; Loscher W., *Biochem. Pharmacol.*, 1982; 31: 837–842; Phillips N., et. al., *Biochem. Pharmacol.*, 1982; 31: 2257–2261). For example, the compound (±)-3-(aminomethyl)-5-methylhexanoic acid, a GAD activator, has the ability to suppress seizures while avoiding the undesirable side effect of ataxia.

It has been discovered that the anticonvulsant effect of isobutyl-GABA is stereoselective. That is, the S-stereoisomer of isobutyl-GABA shows better anticonvulsant activity than the R-stereoisomer. See, for example, Yuen, et. al., in *Bioorganic & Medicinal Chemistry Letters*, 1994; (Vol. 4, No. 6): 823–826. Thus, it would be beneficial to have an efficient process for the synthesis of the S-stereoisomer of isobutyl-GABA.

Presently, (S)-(+)-3-(aminomethyl)-5-methyl hexanoic acid has been prepared by two synthetic routes. These routes each use reactions that require n-butyllithium, and each route contains a step that must be carried out at low temperatures ($\leq -35°$ C.) under carefully controlled conditions. These synthetic routes include the use of (4R,5S)-4-methyl-5-phenyl-2-oxazolidinone as a chiral auxiliary to introduce the stereochemical configuration needed in the final product. See, for example, U.S. Ser. No. 08/064,285, which is hereby incorporated by reference. Although these routes provide the target compound in high enantiomeric purity, they are difficult to conduct on large-scale and use reagents which are either expensive or difficult to handle or both.

The present invention provides an efficient stereoselective method for making the S-stereoisomer of isobutyl-GABA that avoids the above-identified problems and proceeds with fewer steps.

SUMMARY OF THE INVENTION

The present invention provides a method of making (S)-(+)-3-(aminomethyl)-5-methylhexanoic acid which comprises condensing isovaleraldehyde with an alkyl cyanoacetate to form a 2-cyano-5-methylhex-2-enoic acid alkyl ester; reacting the 2-cyano-5-methylhex-2-enoic acid alkyl ester with a dialkyl malonate to form 3-isobutylglutaric acid; forming the anhydride of 3-isobutylglutaric acid; reacting the anhydride with ammonia to form (±)-3-(carbamoylmethyl)-5-methylhexanoic acid; reacting (±)-3-(carbamoylmethyl)-5-methylhexanoic acid with (R)-(+)-α-phenylethylamine to obtain the (R)-(+)-α-phenylethylamine salt of (R)-(−)-3-(carbamoylmethyl)-5-methylhexanoic acid; combining the salt with an acid to obtain (R)-(−)-3-(carbamoylmethyl)-5-methylhexanoic acid; and reacting the (R)-(−)-3-(carbamoylmethyl)-5-methylhexanoic acid with a Hofmann reagent to obtain (S)-(+)-3-(aminomethyl)-5-methylhexanoic acid.

The present invention also provides the novel compounds (±)-3-(carbamoylmethyl)-5-methylhexanoic acid, (R)-(−)-3-(carbamoylmethyl)-5-methylhexanoic acid,(S)-(+)-3-(carbamoylmethyl)-5-methylhexanoic acid, the (R)-(+)-α-phenylethylamine salt of (R)-(−)-3-(carbamoylmethyl)-5-methylhexanoic acid and the (S)-(−)-α-phenylethylamine salt of (S)-(+)-3-(carbamoylmethyl)-5-methylhexanoic acid.

DETAILED DESCRIPTION OF THE INVENTION in accordance with Scheme I below, the present invention provides an efficient stereoselective method for making the S-stereoisomer of isobutyl-GABA.

Scheme I

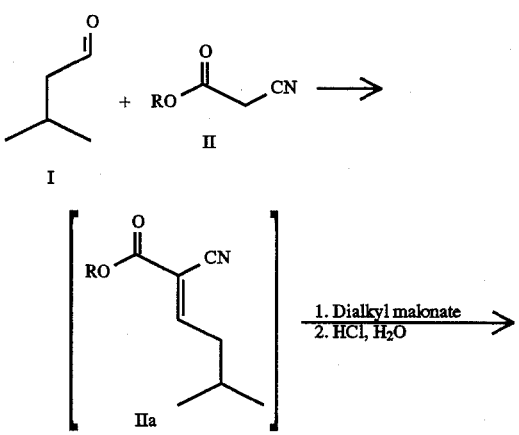

-continued
Scheme I

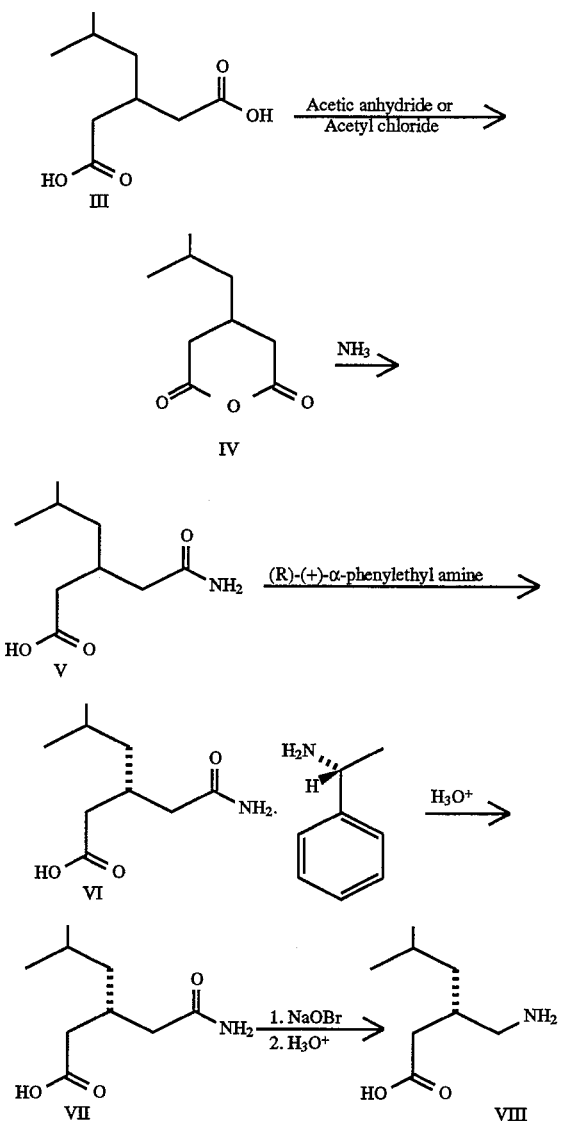

The method of Scheme I generally comprises condensing isovaleraldehyde (I) with an alkyl cyanoacetate (II) to form a 2-cyano-5-methylhex-2-enoic acid alkyl ester (IIa); reacting the 2-cyano-5-methylhex-2-enoic acid alkyl ester with a dialkyl malonate to form 3-isobutylglutaric acid (III); forming the anhydride of 3-isobutylglutaric acid (IV); reacting the anhydride with ammonia to form (±)-3-(carbamoyl methyl)-5-methylhexanoic acid (V); reacting (±)-3-(carbamoylmethyl)-5-methylhexanoic acid with (R)-(+)-α-phenylethylamine to obtain the (R)-(+)-α-phenylethylamine salt of (R)-(−)-3-(carbamoylmethyl)-5-methylhexanoic acid (VI); combining the salt with an acid to obtain (R)-(−)-3-(carbamoylmethyl)-5-methylhexanoic acid (VII); and reacting the (R)-(−)-3-(carbamoylmethyl)-5-methylhexanoic acid with a Hofmann reagent to obtain (S)-(+)-3-aminomethyl-5-methylhexanoic acid (VIII).

In one step of the method, isovaleraldehyde is condensed with an alkyl cyanoacetate to form a 2-cyano-5-methylhex-2-enoic acid alkyl ester. In general, this reaction is carried out in the presence of a base such as di-n-propylamine, diethylamine, diisopropylamine or piperidine, or an acid and base combination such as di-n-propylamine and acetic acid, in an inert solvent such as hexane, heptane, toluene or the like. The term "inert solvent" means a liquid in which a reaction can be carried out that does not detrimentally interact with the starting materials or the products. However, it is noted that the reaction will proceed in the absence of a solvent. In addition, the 2-cyano-5-methylhex-2-enoic acid alkyl ester that is formed can also contain 2-cyano-5-methylhex-3-enoic acid alkyl ester.

The alkyl group, R, in Scheme I, of the alkyl cyanoacetate is preferably a $C_1$–$C_6$ alkyl, branched or straight chain, a $C_3$ to $C_6$ cycloalkyl group or benzyl. Representative examples of $C_1$–$C_6$ alkyl groups include methyl, ethyl, propyl, isopropyl, butyl, isobutyl, tert-butyl, pentyl and hexyl. Representative examples of $C_3$ to $C_6$ cycloalkyl groups include cyclopropyl, cyclobutyl, cyclopentyl and cyclohexyl. Preferably, the $C_1$–$C_6$ alkyl is ethyl.

In general, isovaleraldehyde and alkyl cyanoacetate are combined in an inert solvent with a base and placed under reflux. The water that is liberated is collected azeotropically. When the reaction appears to be complete, the solvent may be removed to yield primarily 2-cyano-5-methylhex-2-enoic acid alkyl ester. In general, the 2-cyano-5-methylhex2-enoic acid alkyl ester that is formed is not isolated or purified and can be used in the next step in crude form. It is noted that the reaction will proceed in the absence of a solvent and that 2-cyano-5-methylhex-3-enoic acid alkyl ester may also be formed in the reaction.

3-Isobutylglutaric acid is made from a 2-cyano-5-methylhex-2-enoic acid alkyl ester by reacting a 2-cyano-5-methylhex-2-enoic acid alkyl ester with a dialkyl malonate followed by hydrolysis and decarboxylation. The alkyl groups of the dialkyl malonate can be the same or different. Examples of suitable alkyl groups include $C_1$–$C_6$ alkyl groups and $C_3$–$C_6$ cycloalkyl groups as defined above and benzyl. A preferred dialkyl malonate is diethyl malonate.

In general, a 2-cyano-5-methylhex-2-enoic acid alkyl ester is reacted directly with the dialkyl malonate and a base. That is, the reaction need not be run in an inert solvent. The reaction mixture can then be added to an acidic aqueous solution such as aqueous sulfuric acid, aqueous hydrochloric acid or aqueous hydrobromic acid, and refluxed to promote hydrolysis and decarboxylation. The progress of the reaction may be monitored by $^1$H-NMR or other methods well known to those skilled in the art, and the 3-isobutylglutaric acid is isolated by methods well known to those skilled in the art. The reaction can be run in a solvent such as hexane, ethanol or methanol. Bases that can be used include, but are not limited to, diethylamine, sodium methoxide, sodium ethoxide, potassium tert-butoxide and di-n-propylamine.

3-Isobutylglutaric acid anhydride can be made from 3-isobutylglutaric acid using methods well known to those skilled in the art for forming the anhydride of an acid. For example, 3-isobutylglutaric acid anhydride can be obtained by refluxing acetyl chloride or acetic anhydride with 3-isobutylglutaric acid and then distilling the mixture. It is noted that the 3-isobutylglutaric acid anhydride need not be isolated and purified, but can be used directly, in crude form, in subsequent steps.

In another step of the method, 3-isobutylglutaric acid anhydride is reacted with ammonia to form (±)-3-(carbamoylmethyl)-5-methylhexanoic acid. In this step, the cyclic anhydride is opened and one of the carbonyl groups is converted to an amide. (±)-3-(carbamoyl methyl)-5-methylhexanoic acid can be recrystallized from a number of solvents including ethyl acetate, water, chloroform and 2-butanone.

The R-stereoisomer of 3-(carbamoylmethyl)-5-methylhexanoic acid can be obtained by reacting (±)-3-(carbamoylmethyl)-5-methylhexanoic acid with (R)-(+)-α-phenylethylamine to form the (R)-(−)-3-(carbamoyl methyl)-5-methylhexanoic acid, (R)-(+)-α-phenylethyl amine salt, which can be isolated. The salt can be recrystallized using various solvents such as chloroform, acetonitrile, ethyl acetate and tetrahydrofuran.

(R)-(−)-3-(carbamoylmethyl)-5-methylhexanoic acid can be obtained by dissolving the salt in water and acidifying the solution. Preferably the resolution is conducted in an organic solvent such as chloroform and less than 1 molar equivalent of the (R)-(+)-α-phenylethylamine is used with respect to the (±)-3-(carbamoylmethyl)-5-methylhexanoic acid.

Alternatively, (R)-(−)-3-(carbamoylmethyl)-5-methylhexanoic acid can be obtained by combining (±)-3-(carbamoylmethyl)-5-methylhexanoic acid with (S)-(−)-α-phenylethylamine in a solution to give the (S)-(−)-α-phenylethylamine salt of (S)-(+)-3-(carbamoylmethyl)-5-methylhexanoic acid, which crystallizes out of the solution leaving the solution enriched in (R)-(−)-3-(carbamoylmethyl)-5-methylhexanoic acid. (R)-(−)-3-(carbamoylmethyl)-5-methylhexanoic acid can then be isolated from the solution by methods well known to those skilled in the art.

In another step of the method, (S)-(+)-3-(aminomethyl)-5-methylhexanoic acid is obtained from (R)-(−)-3-(carbamoylmethyl)-5-methylhexanoic acid via a Hofmann Reaction, which is well known to those skilled in the art. The conditions under which a Hofmann Reaction can be carried out are well known to those skilled in the art, and any such condition known in the art may be used to obtain (S)-(+)-3-(aminomethyl)-5-methylhexanoic acid from (R)-(−)-3-(carbamoylmethyl)-5-methylhexanoic acid. A suitable Hofmann reagent is an alkali metal hypohalite, which can be prepared by combining a base such as sodium hydroxide with a halogen such as bromine. Other alkali metal or alkaline earth metal bases or other halogens can be used. Other Hofmann reagents that can be used include, but are not limited to, I,I-bis(trifluoroacetoxy)-iodobenzene, iodosobenzene with formic acid, [hydroxy(tosyloxy)iodo]benzene, I,I-bis(acetoxy)iodobenzene, lead tetraacetate, benzyltrimethylammonium tribromide, N-bromosuccinimide in basic media (such as potassium hydroxide solution), and N-bromosuccinimide in the presence of mercury (II) acetate or silver acetate.

Isolation of (S)-3-(aminomethyl)-5-methylhexanoic acid after the Hofmann Reaction is carried out is easier than isolating the mixture of enantiomers because sodium chloride or sodium bromide salts tend to crystallize with the product in the case of a mixture of enantiomers. In contrast, in the present method, the chloride or bromide salts do not crystallize with the product. Halide analysis shows about 11% by weight halide (calculated as chloride) in the crude product (unrecrystallized) comprising a mixture of the enantiomers and about 0.1% by weight in the product of the present method.

Moreover, (S)-(−)-3-(carbamoylmethyl)-5-methylhexanoic acid can be easily hydrolyzed under reflux in aqueous hydrochloric acid to give 3-isobutylglutaric acid, which can be used to produce additional (R)-(−)-3-(carbamoylmethyl)-5-methylhexanoic acid.

It is contemplated that the compounds of the present method can be found or isolated in the form of hydrates or solvates, which are considered to fall within the scope of the present invention.

The following examples are intended to illustrate particular embodiments of the invention, and are not intended to limit the specification, including the claims, in any manner.

EXAMPLES

Preparation of 3-Isobutylglutaric acid

A mixture of ethyl cyanoacetate (62.4 g), hexane (70 mL), isovaleraldehyde (52.11 g), and di-n-propylamine (0.55 g) is placed under reflux. Water is collected azeotropically using a water separator. When no additional water is being collected from the reaction, the reaction is cooled and subjected to vacuum distillation to remove the solvent. Diethyl malonate (105.7 g) and di-n-propylamine (5.6 g) are added to the remaining oil (primarily 2-cyano-5-methylhex-2-enoic acid ethyl ester). The mixture is stirred at 50° C. for 1 hour to form 2-cyano-4-ethoxycarbonyl-3-isobutylpentanedioic acid diethyl ester and then poured into an aqueous solution of hydrochloric acid (300 mL of 6N). The mixture is placed under reflux. The reaction is maintained under reflux until $^1$H-NMR indicates that the hydrolysis and decarboxylation are complete (approximately 72 hours). The reaction is cooled to 70°–80° C. and the aqueous mixture is extracted with toluene (1×250 mL, 1×150 mL). The toluene extracts are combined and the solvent is removed by distillation to give 88.7 g of 3-isobutylglutaric acid as an oil. When purified 3-isobutylglutaric acid is a solid with a melting point in the range of about 40° C. to about 42° C. $^1$H NMR (CDCl$_3$, 200 MHz): δ0.92 (d, 6H, J=6.6 Hz), 1.23 (dd, 2H, J$_1$=6.6 Hz, J$_2$=6.5 Hz), 1.64 (m, 1 H), 2.25–2.40 (m, 1 H), 2.40–2.55 (m, 4 H). $^{13}$C NMR (CDCl$_3$): δ22.4, 25.1, 29.5, 38.4, 43.4, 179.2 IR (KBr): 680.7, 906.4, 919.9, 1116.6, 1211.1, 1232.3, 1249.6, 1301.7, 1409.7, 1417.4, 1448.3, 1463.7, 1704.8, 2958.3, 3047.0 cm$^{-1}$.

Preparation of 3-Isobutylglutaric acid anhydride

3-Isobutylglutaric acid (156 g) and acetyl chloride (130 g) are combined and placed under reflux for 16 hours. The mixture is distilled at atmospheric pressure until a distillate reflux temperature of 135° C. is reached. The mixture is then cooled and placed under vacuum distillation to give 129 g of 3-isobutylglutaric acid anhydride (boiling point 127°–128° C., 1 mm Hg). $^1$H-NMR (CDCl$_3$, 200 MHz): δ0.91 (d, 6H, J=6.6 Hz), 1.20–1.24 (m, 2H), 1.52–1.78 (m, 1H), 2.10–2.45 (m, 3H), 2.79–2.91 (m, 2H). $^{13}$C-NMR (CDCl$_3$, 50 MHz): δ166.53, 43.99, 36.48, 26.79, 25.08, 22.57. IR (neat): 559.3, 592.0, 609.4, 659.5, 837.0, 954.6, 1033.7, 1070.3, 1184.1, 1241.9, 1288.2, 1369.2, 1388.5, 1411.6, 1425.1, 1469.5, 1760.7, 1810.8, 2873.4, 2958.3, 3552.2 cm$^{-1}$.

Preparation of (+)-3(Carbamoylmethyl)-5-methylhexanoic acid

Aqueous ammonia (308 g of 28% ammonium hydroxide, 5.06 mol), water (431 g), and methyl tert-butyl ether (200 g) are combined and cooled to 15° C. 3-Isobutylglutaric acid anhydride is added and the reaction mixture is allowed to warm to 50° to 60° C. The reaction mixture is cooled to 20°–25° C. The solvent is evaporated and the pH of the solution is adjusted to 1.0 with concentrated hydrochloric acid. Water (200 mL) is added and the mixture is filtered. The solid is washed with water (200 mL). The solid is dried under reduced pressure to give 408 g of (±)-3-(carbamoylmethyl)-5-methylhexanoic acid as an off-white solid. (±)-3-(Carbamoylmethyl)-5-methylhexanoic acid has a melting point in the range of about 107.5° to about 108.5° C. $^1$H-NMR (DMSO-d6, 200 MHz): δ0.84 (d, 6H, J=6.5 Hz), 1.07–1.17 (m, 2H), 1.50–1.72 (m, 1H), 1.98–2.25 (m, 5H), 6.75 (s, 1H), 7.30 (s, 1H), 11.6 (s, 1H). IR (KBr): 592.0, 655.7, 700.0, 1010.5, 1133.9, 1214.9, 1241.9, 1278.6, 1294.0, 1427.1, 1461.8, 1585.2, 1668.1, 1700.9, 2514.7, 2622.7, 2962.1, 3220.5, 3367.1 cm$^{-1}$.

Preparation of (±)-3-(Carbamoylmethyl)-5-methylhexanoic acid (without isolation and purification 3-isobutylglutaric acid anhydride)

3-Isobutylglutaric acid (68.8 kg) and acetic anhydride (44.5 kg) are combined and placed under reflux for 2.5 hours. The mixture is placed under atmospheric distillation followed by vacuum distillation to remove acetic acid and acetic anhydride. The undistilled 3-isobutylglutaric acid anhydride is dissolved in methyl tert-butyl ether (63 kg) and added to a solution of aqueous ammonia (49 kg of 28% ammonium hydroxide) and water (92 kg) at a temperature of 25° C. or less. The mixture is stirred for 35 minutes and the layers are separated. The aqueous layer is placed under vacuum distillation to remove any remaining volatile non-aqueous solvent. Concentrated hydrochloric acid (51 kg) is added to the aqueous mixture to obtain a pH of 1.5. The mixture is cooled to 0°–10° C. and filtered. The solid is washed with water (50 L) and dried under reduced pressure. The solid is then dissolved in hot (70° C.) ethyl acetate (237 kg) and filtered. The solution is cooled to 0°–5° C. and the product is collected by filtration. The solid is washed with cold ethyl acetate (45 kg) and dried under reduced pressure to give 47.5 kg of (±)-3-(carbamoylmethyl)-5-methylhexanoic acid as an off-white solid having a melting point in the range of 106° to about 108° C.

Preparation of (R)-(−)-3-(Carbamoylmethyl)-5-methylhexanoic acid, (R)-(+)-α-phenylethylamine salt (±)-3-(Carbamoylmethyl)-5-methylhexanoic acid (17.0 g) is placed in chloroform (292 g) and ethanol (3.2 g) is added. The mixture is heated to 55° C. and (R)-(+)-α-phenylethylamine (6.0 g) is added. After a solution forms additional (R)-(+)-α-phenylethylamine (2.0 g) and (R)-(−)-3-(carbamoylmethyl)-5-methylhexanoic acid seed crystals (50 mg) are added. The mixture is cooled to 32° C. and filtered. The solid is washed with chloroform (30 mL). The solid is dried under reduced pressure to give 10.5 g of the (R)-(+)-α-phenylethylamine salt of (R)-(−)-3-(carbamoylmethyl)-5-methylhexanoic acid as a white solid having a melting point in the range of about 123° C. to about 126° C. $^1$H-NMR (DMSO-d6, 200 MHz): δ0.83 (d, 6H, J=6.4 Hz), 1.1–1.4 (m, 2H), 1.32 (d, 3H, 6.6 Hz), 1.50–1.75 (m, 1H), 2.0–2.3 (m, 5H), 4.11 (q, 1H, J=6.6 Hz), 6.0 (s, (broad), 3H), 6.72 (s, 1H), 7.2–7.5 (m, 6H). IR (KBr): 700.0, 763.7, 1091.5, 1270.9, 1400.1, 1523.5, 1633.4, 1660.4, 2869.6, 2933.2, 2956.3, 3187.8, 3376.7 cm$^{-1}$. Chiral HPLC: (Chiralcel OD-H (Chiral Technologies, Inc., Exton, Pa.) Hexane/isopropanol/formic acid, 96: 4: 0.1) enantiomeric purity >99% (R)-(−)-3-(carbamoylmethyl)-5-methylhexanoic acid Preparation of (R)-(−)-3-(Carbamoylmethyl)-5-methylhexanoic acid The (R)-(+)-α-phenylethylamine salt of (R)-(−)-3-(carbamoylmethyl)-5-methylhexanoic acid (10.9 g) is placed in water (35 mL). The mixture is acidified to pH 1.7 at 31° C. with concentrated hydrochloric acid. The mixture is cooled to 4° C. and filtered. The solid is washed with cold (4° C.) 1M hydrochloric acid (10 mL) and dried under reduced pressure to give 6.2 g of (R)-(−)-3-(carbamoylmethyl)-5-methylhexanoic acid as a white solid having a melting point in the range of about 130° C. to about 133° C. $^1$H-NMR (DMSO-d6, 200 MHz): δ0.84 (d, 6H, J=6.5 Hz), 1.09–1.15 (m, 2H), 1.50–1.65 (m, 1H), 2.01–2.27 (m, 5H), 6.76 (s, 1H), 7.30 (s, 1H), 12.0 (s, 1H). IR (KBr): 624.8, 954.6, 1168.7, 1207.2, 1236.1, 1294.0, 1411.6, 1592.9, 1643.1, 1712.5, 2873.4, 2931.3, 2958.3, 3224.4, 3332.4, 3434.6 cm$^{-1}$. Chiral HPLC: (Chiralcel OD-H, Hexane/isopropanol/ formic acid, 96/4/0.1) enantiomeric purity >99% (R)-(−)-3-(carbamoylmethyl)-5-methylhexanoic acid Preparation of (S)-(+)-3-Aminomethyl-5-methylhexanoic acid (R)-(−)-3-(carbamoylmethyl)-5-methylhexanoic acid (30 g) is dissolved in water (28 g) and 50% sodium hydroxide solution (12.6 g) and cooled to 5° C. In a separate flask water (85 g), 50% sodium hydroxide solution (53 g), and bromine (30.6 g) are combined while maintaining a temperature of less than 10° C. The bromine solution is added to the solution of (R)-(−)-3-(carbamoylmethyl)-5-methylhexanoic acid and warmed until a temperature of 80° C. is reached. The solution is cooled to 45° C. and quenched into 37% hydrochloric acid solution (42 g). The mixture is heated to 89° C. and then cooled to 3° C. The mixture is filtered and the solid is washed with water (30 mL). The solid is dried under reduced pressure to give 16.7 grams of (S)-(+)-3-aminomethyl-5-methylhexanoic acid.

HPLC enantiomer determination: Derivative with 1-fluoro-2,3-dinitrophenyl-5-L-alanine amide (Hypersil BDS (from Keystone Scientific, Inc., Bellefonte, Pa.), 0.05M triethylamine (adjusted to pH 3 with phosphoric acid)/acetonitrile, 62/38) enantiomeric purity 99.8% (S)-(+)-3-aminomethyl-5-methylhexanoic acid.

The solid (16.3 g) is recrystallized from a mixture of isopropanol (54 g) and water (54 g) to give 14.7 g of recrystallized (S)-(+)-3-aminomethyl-5-methylhexanoic acid having a melting point in the range of about 184° C. to about 186° C.—decomposes. $^1$H-NMR (D$_2$O, 200 MHz): δ0.88 (d, 3H, J=6.5 Hz), 0.90 (d, 3H, J=6.5 Hz), 1.21 (t, 2H, J=7 Hz), 1.52–1.75 (m, 1H), 2.1–2.4 (m, 3H), 2.89–3.06 (m, 2H). IR (KBr): 700.0, 823.5, 860.1, 1278.6, 1334.5, 1369.2, 1417.4, 1645.0, 2210.0, 2603.4, 2690.2, 2775.1, 2844.5, 2873.4, 2896.6, 2923.6, 2956.3 cm$^{-1}$.

Preparation and Resolution of (R)-(−)-3-(Carbamoylmethyl)-5-methylhexanoic acid followed by regeneration of 3-isobutylglutaric acid from (S)-(−)-3-(carbamoylmethyl)-5-methylhexanoic acid (±)-3-(carbamoylmethyl)-5-methylhexanoic acid (47 kg, 251 mol) is placed in chloroform (807 kg) and ethanol (8.8 kg). The mixture is heated to 55° C. and (R)-(+)-α-phenylethylamine (16.7 kg) is added. After a solution forms additional (R)-(+)-α-phenylethylamine (5.5 kg) and (R)-(−)-3-(carbamoylmethyl)-5-methylhexanoic acid seed crystals (100 g) are added. The mixture is cooled to 32° C. and filtered. The solid is washed with chloroform (100 kg) and dried under reduced pressure to give the (R)-(+)-α-phenylethylamine salt of (R)-(−)-3-(carbamoylmethyl)-5-methylhexanoic acid. The solid is dissolved in water (138.5 kg) and concentrated hydrochloric acid (9.4 kg) is added. The mixture is cooled to 0°–10° C. and filtered. The solid is washed with cold water (20 L) and dried under reduced pressure to give 17.7 kg of (R)-(−)-3-(carbamoyl methyl)-5-methylhexanoic acid as a white solid.

The chloroform filtrate is extracted with aqueous sodium hydroxide solution (25 kg 50% sodium hydroxide dissolved in 106 kg water). The aqueous extract is acidified with concentrated hydrochloric acid (94 kg) and heated under reflux for approximately 24 hours. The aqueous mixture is extracted with methyl tert-butyl ether (70.5 kg). The methyl tert-butyl ether solution is concentrated under reduced pressure to give 3-isobutylglutaric acid (27.4 kg).

We claim:

1. The compound (±)-3-(carbamoylmethyl)-5-methylhexanoic acid.

2. The compound (R)-(−)-3-(carbamoylmethyl)-5-methylhexanoic acid.

3. The compound (S)-(+)-3-(carbamoylmethyl)-5-methylhexanoic acid.

4. The compound that is the (R)-(+)-α-phenylethylamine salt of (R)-(−)-3-(carbamoylmethyl)-5-methylhexanoic acid.

5. The compound that is the (S)-(−)-α-phenylethylamine salt of (S)-(+)-3-(carbamoylmethyl)-5-methylhexanoic acid.

* * * * *